United States Patent
Parenti

[11] Patent Number: 5,724,093
[45] Date of Patent: Mar. 3, 1998

[54] APPARATUS FOR THE OPTICAL DETECTION OF SURFACE DEFECTS, PARTICULARLY IN ROLLED STRIPS

[75] Inventor: Riccardo Parenti, Genoa, Italy

[73] Assignee: Finmeccanica S.p.A. Azienda Ansaldo, Genoa, Italy

[21] Appl. No.: 587,365

[22] Filed: Jan. 16, 1996

[30] Foreign Application Priority Data

Feb. 24, 1995 [IT] Italy ................. MI95A0363

[51] Int. Cl.$^6$ ................. H04N 7/18; H04N 9/47
[52] U.S. Cl. ................. 348/131; 348/92; 356/237
[58] Field of Search ................. 348/79, 92, 93, 348/128, 131; 356/237, 394, 371; H04N 7/18, 9/47

[56] References Cited

U.S. PATENT DOCUMENTS

| | | | |
|---|---|---|---|
| 4,449,818 | 5/1984 | Yamaguchi et al. | 348/128 |
| 4,538,909 | 9/1985 | Bible et al. | 356/237 |
| 5,058,178 | 10/1991 | Ray | 3456/237 |
| 5,278,012 | 1/1994 | Yamanaka et al. | 356/237 |
| 5,396,334 | 3/1995 | Sugawara | 356/237 |
| 5,455,870 | 10/1995 | Sepai et al. | 356/237 |
| 5,497,234 | 3/1996 | Haga | 356/237 |

Primary Examiner—Tommy P. Chin
Assistant Examiner—Nhon T. Diep
Attorney, Agent, or Firm—Kalow, Springut and Bressler

[57] ABSTRACT

An apparatus for detecting surface defects particularly in rolled strips, the operation of the apparatus being based on the use of a telecamera with multiple sensitive elements which form parts of respective bright-field and dark-field recording channels. More precisely, the above-mentioned elements are sensitive to light radiations within respective ranges of wavelengths corresponding to those of the radiations emitted by the light sources. The latter are arranged in a manner such that, in one case, the radiation emitted thereby falls substantially tangential on the surface of the strip to be checked and, in the other case, such that the radiation reflected by the said surface is directed towards the telecamera. From a comparison of the images recorded by the recording channels, the comparison being effected by electronic circuit provided in the apparatus, it is possible to derive full information on the state of the surface under examination and hence to apply any necessary modifications to the production cycle.

6 Claims, 3 Drawing Sheets

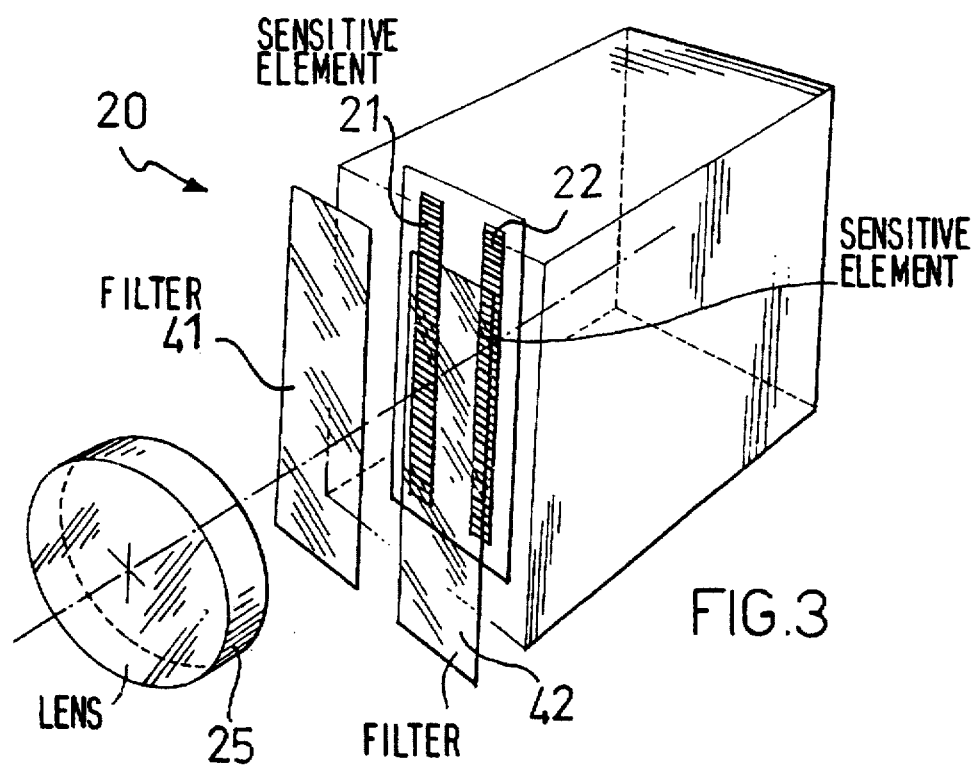
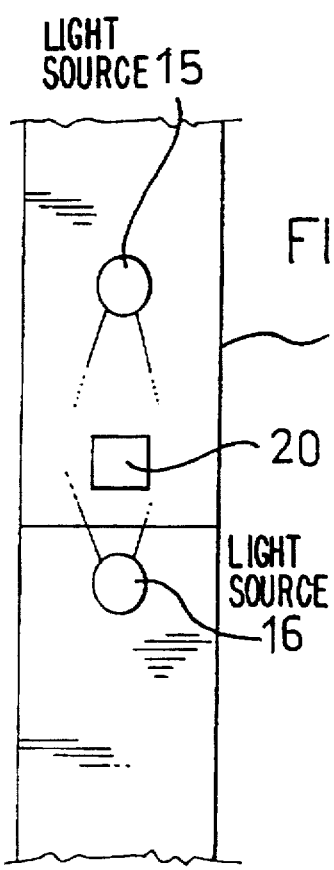
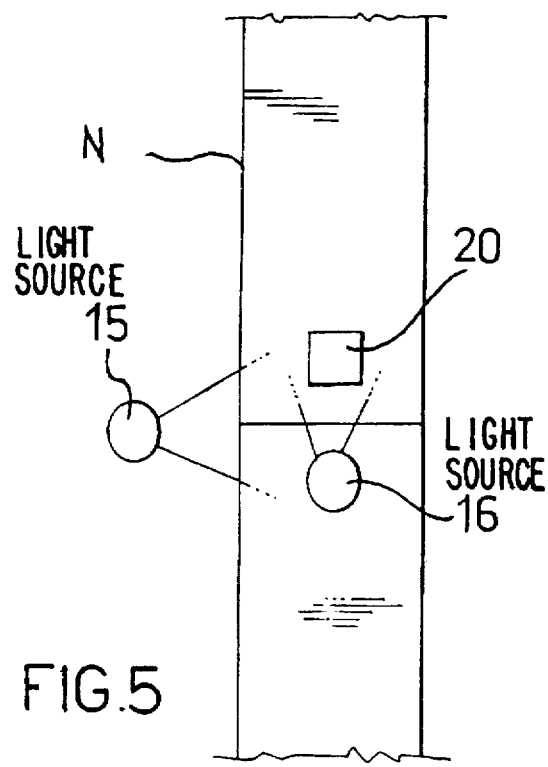

APPARATUS FOR THE OPTICAL DETECTION OF SURFACE DEFECTS, PARTICULARLY IN ROLLED STRIPS

FIELD OF THE INVENTION

The present invention relates to an apparatus for the optical detection of defects in a surface by video recordings made by a bright-field channel and a dark-field channel and processed by electronic means included in the apparatus.

BACKGROUND OF THE INVENTION

Before explaining further defining the above-mentioned invention, it is useful to state beforehand that the apparatuses to which it relates are already used in strip-rolling processes in the iron and steel industry; they are foreseen it is devoted mainly for production quality-control by the detection and transmission of informations relating to the surface analysis of the products processed.

In fact, these informations can be processed, classified, and studied to enable all of the necessary corrections to be applied to the production cycle in order to achieve the desired results.

For this purpose, the known apparatuses generally have a pair of conventional telecameras connected to an electronic system for the control and processing of the images, and are disposed adjacent an end portion of the strip being processed; more precisely, the strip is preferably moved over a roll which is raised relative to the rest of the rolling mill (see the diagram of FIG. 1) to facilitate the installation of first and second telecameras C1 and C2 included in a bright-field recording channel and a dark-field recording channel, respectively, for acquiring the images.

Moreover, a light source L is provided for illuminating the surface of the strip on the raised roll.

The two telecameras C1 and C2 view the same portion of the path over the raised roller of the strip being processed, at two different angles; more precisely, the first one operates in a direction almost tangential to the curvature of the strip on the aforementioned roller, the dark-field channel being preferred for this purpose, whereas the other operates in a direction close to the angle of reflection of the light striking the strip and is the bright-field channel.

After digital conversion, the images coming from the telecameras are processed electronically by the control system and are then combined to provide the desired result relating to the state of the surface to be checked.

Specific algorithms are used for this purpose and will depend upon the type of check to be carried out, upon the electronic instrumentation used, etc., at the time in question.

In practice, the task of the dark-field channel is essentially to provide an image produced as a result of the surface irregularities found on the strip by light skimming its surface, in fact providing a confirmation of the surface defects found by the light-field channel.

It is hardly necessary to state that, although they are not shown in the schematic representation of FIG. 1, the electronic means for carrying out the functions described briefly above are present in the apparatus; these electronic means, or some of them, may be arranged, together with the telecameras and the light sources, on a conventional support structure not shown in FIG. 1, for simplicity. The main problems connected with apparatuses of this type are due essentially to the difficulty of having a stable angular arrangement between the recording directions of the two telecameras; as has in fact already been stated, the two telecameras view, in a fixed manner, the same portion of the path of the strip being rolled; the telecameras must not therefore undergo changes in their relative positions during the various stages of the processing. This would in fact not permit the use of the dark-field channel as a check for the detections made by the bright-field channel; in fact, it must be remembered that, owing to their intrinsic technological characteristics and the distance at which they generally operate, the telecameras C1 and C2 can view and focus only a limited region of strip on which the surface checking is to be carried out.

As a result of the environmental conditions in which they work, however, (for example, on account of the temperatures which may be used in rolling processes with consequent thermal expansion, or of the vibrations which are produced by a rolling mill in operation), it is almost inevitable that the relative positions of the two telecameras will undergo changes thus reducing the performance of the apparatus, sometimes in an unacceptable manner.

SUMMARY OF THE INVENTION

The object of the present invention is to provide a detection apparatus of the type considered above having structural and functional characteristics such as to overcome the problems mentioned with reference to the current state of the art as it is understood from the foregoing. In other words, the apparatus should have characteristics of operative simplicity and flexibility such as to enable it to operate reliably even in external conditions which are not ideal.

This object is achieved by an apparatus as defined in the first of the following claims.

DESCRIPTION OF THE DRAWINGS

For a better understanding of further aspects of the invention, an embodiment thereof is described below and illustrated in the appended drawings, provided by way of non-limiting example; in particular, in the drawings:

FIG. 3 shows a detail of the apparatus of FIG. 2, FIGS. 4 and 5 show corresponding plan views of the apparatus of FIG. 2 and of a variant thereof, respectively.

DESCRIPTION OF THE PREFERRED EMBODIMENT

Figure 1:
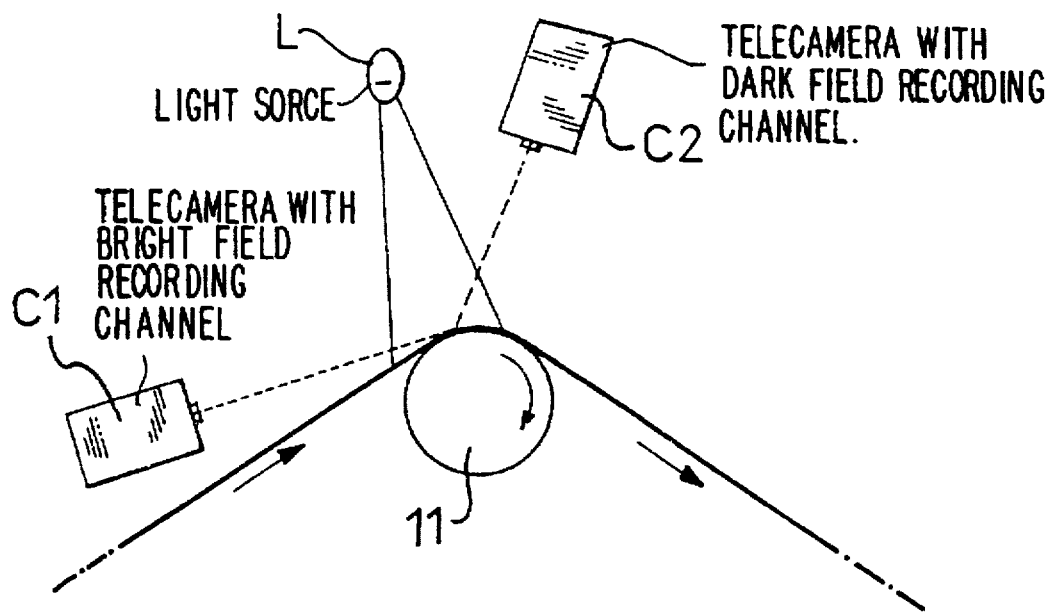
FIG. 1 shows, as already stated, an example of apparatus according to the prior art.

With reference, therefore, to FIGS. 2–5, these show an apparatus 10 according to the invention disposed adjacent a raised roll 11 of a rolling mill; this equipment is mounted on a suitable structure which, for simplicity, has not been shown in the drawings. More particularly, the equipment includes two light sources 15 and 16 which emit light with respective wavelengths within respective ranges of certain amplitudes, corresponding to different colours; the first source 15 emits light rays which skim the surface of the strip N when it passes through the detection region over the roll 11, whilst the second source 16 emits light rays which are reflected by the surface of the strip N in the said detection region.

It can be seen from a comparison with FIG. 1 that, in this embodiment, the light sources are located in positions substantially corresponding to those of the telecameras of the prior art.

The apparatus 10 comprises a telecamera 20 of the type with two linear sensitive elements 21 and 22, which is shown only schematically in FIG. 3 in which the positions of some of its parts are shown relative to a lens 25; the telecamera is of the high-speed, high-resolution colour scanning type having CCD components and is already used in industrial applications and generally known under the English definition "high-speed, high-resolution CCD colour scan camera".

The telecamera views the surface of the strip to be checked in a direction substantially perpendicular thereto.

Filters 41 and 42 are also provided, adjacent the lens 25 of the telecamera 20, for each of the sensitive elements; the sensitive element 21 and the filter 41 associated therewith form parts of a bright-field recording channel C1 and the element 22 and the filter 42 are included in a dark-field recording channel C2. Moreover, each of the elements 21 and 22 is sensitive to light radiation in a respective wavelength range corresponding to that of the radiation emitted by one of the sources 15 and 16.

The equipment of the invention also includes electronic means, not shown in the drawings, which can process the images coming from the bright-field and dark-field channels C1 and C2 to provide the desired results of the checking.

With reference to the structure described up to now, the invention operates in the following manner.

The two light sources 15 and 16 emit light of different colours, for example, red and green, intended for the respective recording channels C1 and C2; more precisely, the source 15 illuminates the detection region of the path of the strip viewed by the telecamera with light having a low trajectory and intended for the dark-field channel C2 whilst the source 16 illuminates the same region at an angle such as to enable the red light rays emitted thereby and intended for the bright-field channel C1 to be reflected towards the aforesaid telecamera.

The effect of the filters 41 and 42 in the telecamera is to screen the respective sensitive elements associated therewith from the light radiation which comes from the region to be checked but does not have the corresponding wavelength; in practice, therefore, by virtue of the effect of the filters, the reflected red light emitted by the light source 16 will not strike the sensitive element associated with the dark-field channel and, conversely, the sensitive element associated with the light-field channel will not be affected by the green light emitted with a low trajectory by the source 15.

It can be understood that, by this measure, it is possible, essentially, to produce a scheme for detecting surface defects which is functionally equivalent to that of the considered prior art: that is to say, this embodiment also has a dark-field channel for checking detections carried out by the recordings made with the bright-field channel. Naturally, the processing of the images by the electronic means will involve the preparation of suitable algorithms which will depend upon the type of checking to be carried out, upon the relative positions of the sources 15 and 16, upon their luminous intensity, upon the distance of the telecamera from the detection region, upon the type of surface, etc. etc.

However, unlike the prior art, the present invention can overcome the problem caused by changes in the relative positions of the two video cameras by virtue of the use of two light sources and a single telecamera with two sensitive elements.

In fact, it can be seen that, by emitting the light radiation from the two sources 15 and 16 with respective cones of light of suitable angular amplitude (visible in FIGS. 2, 4 and 5), that is, with amplitudes which will depend upon various factors such as the type of surface to be checked (which in turn is connected with the curvature, the roughness of the strip, etc. etc) the distances of the sources therefrom, the light intensity, etc., it is in any case possible to ensure that the light rays strike the detection region of the strip viewed by the telecamera even after any movements of the equipment due to the environmental conditions already mentioned.

The telecamera with multiple sensitive elements also enables the dark-field and bright-field channels to be fixed together and therefore not subject to relative movements. Finally, it can be seen that the filters 41 and 42 ensure optimal operation of the telecamera and of its sensitive elements even with variations in the conditions of illumination of the strip owing to the movements of the equipment already mentioned.

Naturally, it is not difficult to think of possible variations which could be applied to the equipment described up to now, possibly intended to improve the embodiment described above and the performance of the apparatus of the invention. For example, it would not be difficult to design an apparatus in which both the telecamera and the light sources are mounted on adjustable supports operatively linked to an electronic control system which could adjust their relative positions.

A similar solution could be useful for applications other than that seen above, in which the surface to be checked has variable curvature and not uniform curvature as in the case of the rolled strip. For example, an item such as a car or other vehicle door might be considered; this would be checked by an apparatus according to the invention in which the telecamera and the light sources could check the points of the surface by performing movements correlated with the shape of the item and coordinated with one another by an electronic processor program.

Moreover, the telecamera 20 could be of the type with more than two sensitive elements to enable the apparatus to be used in applications with more than two colours.

Furthermore, the use of light sources which emit radiation focused, for example, by suitable focusing means such as lenses or the like should not be excluded in some applications, for instance, those in which the distance between the telecamera and the surface to be checked permits it or when checking stationary surfaces. For example, an embodiment in which a source of focused rays which are reflected by the surface onto a single sensitive element might be considered, naturally, the system would, in any case, need to have conditions of stability such that the emission of the rays in a cone as referred to adore and shown in FIG. 2 are not necessary.

Figure 2:
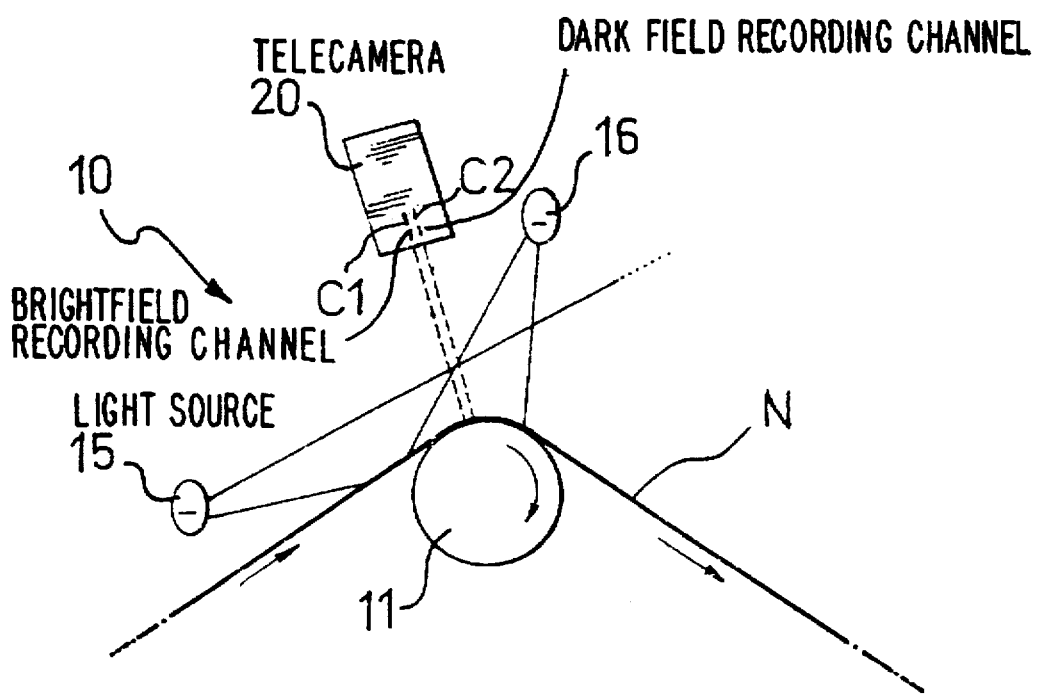
FIG. 2 shows schematically a first embodiment of apparatus according to the invention.

It just matters to point out that the arrangement of the light sources relative to the path of the strip being rolled could also differ from that shown in FIG. 2 and, in this connection, a possible variant is shown in FIG. 5.

It can easily be seen in this drawing and also by comparing it with FIG. 4, which is the plan view of the embodiment considered above, that the light source 15 may be disposed beside the strip being rolled.

More generally, it can be stated that the fact that the arrangement of the light sources can be changed represents a further advantage deriving from the functional flexibility of the invention, in fact it is clear that, since the light sources can be arranged in various positions, naturally taking account of the need for correct illumination to permit recording by the telecameras, the apparatus of the invention can be adapted to different logistical and operative conditions which may arise from time to time.

In this connection, it should be noted that, with sources which emit radiation in perpendicular or, more generally, intersecting directions, it is possible to use different polarizations of the light for the radiation emitted instead of or in addition to the colour differentiation already considered. In other words, therefore, the introduction of the use of more than one light source in the invention also enables use to be made of any optical phenomena which these can achieve in addition to the polarization already mentioned, such as interference or composition phenomena of light radiation.

As already mentioned, the use of more than two light sources should not be excluded; naturally, this alternative involves the need to be able to adapt the apparatus of the invention, for example, by increasing the number of sensitive elements of the video camera, again taking account of the teaching provided in the description given above.

Figure 6:
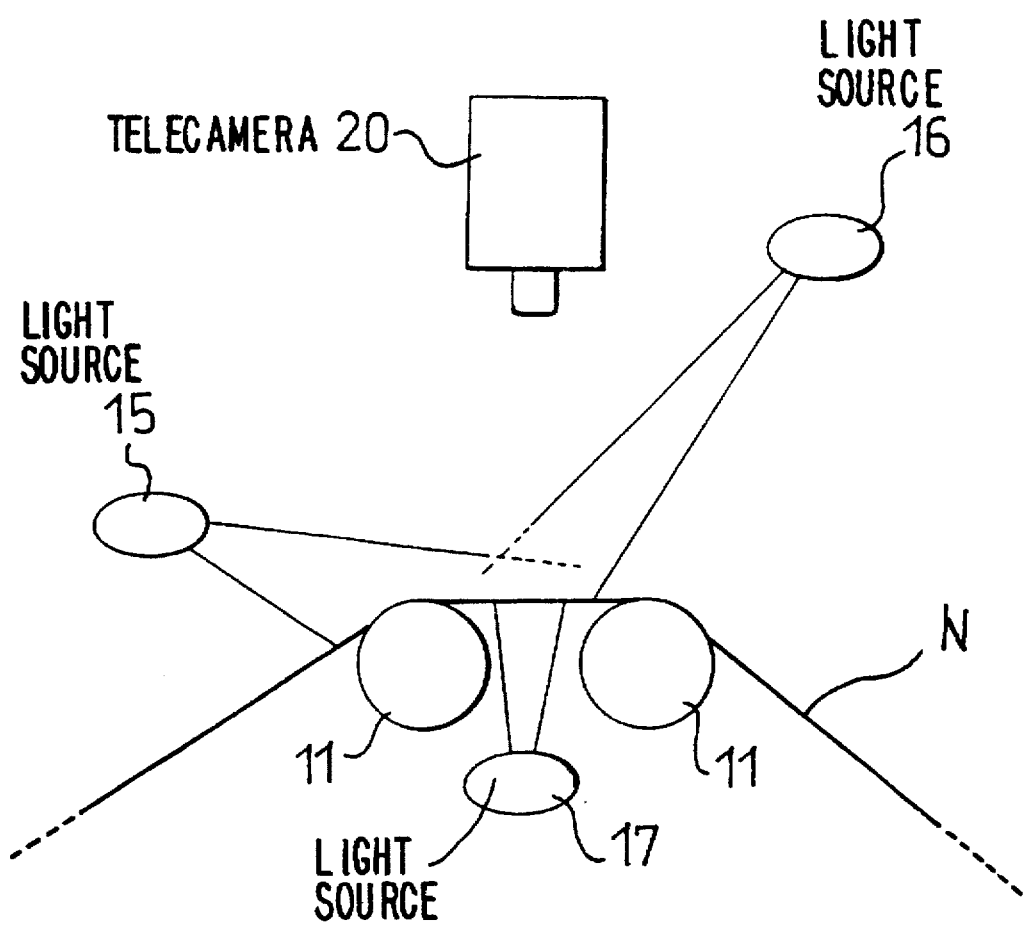
FIG. 6 shows a further variant of the invention.

A similar alternative would be advantageous for the detection of through-holes in the strip; in fact, as shown in FIG. 6, by arranging a monitoring region of the strip between two successive rollers, it is possible to locate a third light source 17 on the opposite side of the strip to the other two, for emitting radiation in a third wavelength range different from the previous ranges; in this case, the colour blue has been used.

In this variant, for the explanation of which, the same numerals have been used as those of the previous embodiment for the common elements already described, the telecamera 20 has a third sensitive element and a filter associated therewith which form parts of a third recording channel C3 similar to those already seen above.

As regards its operation, in this variant of the invention, the third light source emits radiation towards the telecamera 20 and it can therefore be understood that, when a through-hole in the strip passes in front of the third light source, the radiation emitted thereby will be picked up by the third channel C3, thereby providing further information which can be processed by the electronic means of the apparatus thereby ensuring more complete monitoring of the strip.

Finally, the use of the apparatus described on rolled metal strips should in any case not limit the field of application of the invention, the advantageous use of which in other industrial sectors affected by the same problems relating to the checking of surface defects and the quality-control of strips should not be excluded; other possible fields of use could be, for example, those of the production of reels of paper or of plastics films.

I claim:

1. Apparatus for the optical detection of defects in a surface, by video recordings made through a bright-field channel and a dark-field channel, processed by electronic means included in the apparatus, comprising:
    a telecamera having at least two sensitive elements, each of which is sensitive to light radiations of a respective wavelength range and is included in one of the bright-field and dark-field recording channel, the telecamera viewing a surface to be checked in a direction substantially perpendicular thereto, and further comprising first and second light sources which emit, onto the surface to be checked, light radiations with respective wavelengths corresponding to those with which the aforesaid sensitive elements operate, one of said light sources emitting radiations substantially tangential to the surface to be checked and the other source emitting radiations that are reflected by the surface towards the telecamera.

2. Apparatus according to claim 1, wherein the telecamera has filters associated with the respective sensitive elements for filtering out the light radiations of wavelengths not corresponding to those with which the sensitive element associated to the filter operates.

3. Apparatus according to claim 1 comprising a third light source arranged on the side of the surface opposite to that of the other two light sources for emitting light radiation in a respective wavelength range different from the previous ranges towards the telecamera, the telecamera also comprising a third element sensitive to the radiation emitted by the third light source and forming part of a third recording channel of the apparatus.

4. Apparatus according to claim 1 wherein the light radiations emitted by said first and second light sources have respective different polarizations.

5. Apparatus according to claim 1, wherein the telecamera is a high-speed, high-resolution CCD colour scan telecamera and said surface is moving relative to said apparatus.

6. Apparatus according to claim 3 wherein the light radiations emitted by at least two of said light sources, have respective different polarizations.

\* \* \* \* \*